United States Patent [19]
Kim et al.

[11] Patent Number: 5,703,142
[45] Date of Patent: Dec. 30, 1997

[54] PHOTO-CURABLE PREPOLYMER COMPRISING QUATERNARY AMMONIUM SALT AND PROCESS FOR PREPARING THEREOF

[75] Inventors: Sang-Keun Kim; Haeng-Woo Lee; Cheol-Kyu Choi, all of Yousung-Ku; Jeong-Deuk Kim, Seoul; Jin-Who Hong; Chang-Soo Kim, both of Kyonggi-do; Kong-Hyun Whang, Seoul, all of Rep. of Korea

[73] Assignee: Hanwha Chemical Corporation, Seoul, Rep. of Korea

[21] Appl. No.: 534,713

[22] Filed: Sep. 27, 1995

[30] Foreign Application Priority Data

Sep. 27, 1994 [KR] Rep. of Korea ............... 94-24337

[51] Int. Cl.$^6$ ................................................ C08F 2/46
[52] U.S. Cl. ........................... 522/90; 522/174; 522/175
[58] Field of Search ........................... 522/90, 174, 175

[56] References Cited

U.S. PATENT DOCUMENTS 3,933,697  1/1976  Fujii et al. ........................ 521/159
5,075,345  12/1991 Mayer et al. ...................... 521/159

FOREIGN PATENT DOCUMENTS 0541289  5/1993  European Pat. Off. .

OTHER PUBLICATIONS

Radtech Asia '93 (pp. 492–498, Nov. 10–13, 1993).

*Primary Examiner*—Mark Chapman
*Attorney, Agent, or Firm*—Birch, Stewart, Kolasch & Birch, LLP

[57] ABSTRACT

The present invention relates to a photo-curable prepolymer having the following formula (I):

$$W \begin{cases} \left[ (CH_2)_6-NH-\overset{O}{\underset{\|}{C}}-O-R'_1-O-\overset{O}{\underset{\|}{C}}-\underset{R_1}{\overset{|}{C}}=CH_2 \right]_a \\ \left[ (CH_2)_6-NH-\overset{O}{\underset{\|}{C}}-O-R'_2-O-\overset{O}{\underset{\|}{C}}-\underset{R_1}{\overset{|}{C}}=CH_2 \right]_b \\ \left[ (CH_2)_6-NH-\overset{O}{\underset{\|}{C}}-O-R'_3-O-\overset{O}{\underset{\|}{C}}-\underset{R_1}{\overset{|}{C}}=CH_2 \right]_c \end{cases} \quad (I)$$

in which

W represents

[structure: six-membered ring with three N atoms and three C=O groups]

$R_1$ represents hydrogen or methyl;
$R_1'$ represents $$\left[ -(CH_2)_n-\underset{R_2}{\overset{R_2\ X^-}{\underset{|}{\overset{|}{N^+}}}}-(CH_2)_o- \right],$$

$$\left[ -(CH_2)_p-\underset{(CH_2)_q-\underset{R_2}{\overset{R_2\ X^-}{\underset{|}{\overset{|}{N^+}}}}-R_2}{\overset{|}{CH}}-(CH_2)_o- \right],$$

$$\left[ -(CH_2)_n-\underset{\text{(piperidinium ring)}}{N^+}-(CH_2)_o- \right] X^-, \text{ or}$$

$$\left[ -(CH_2)_p-\underset{(CH_2)_q-N^+-\text{morpholinium}}{\overset{|}{CH}}-(CH_2)_o- \right] X^-$$

wherein X represents chlorine or bromine atom, $R_2$ represents methyl or ethyl, n, o and q independently of one another denote an integer of 1 to 6 and p denotes an integer of 0 to 6;

$R_2'$ and $R_3'$ are identical to or different from each other and represent $$-CH_2-\underset{CH_3}{\overset{|}{CH}}-,$$

$$-CH_2-CH_2-CH_2-CH_2-,$$
$$-CH_2-CH_2+OCH_2CH_2\overset{}{)_L}$$

wherein L denotes an integer of 0 to 5, or $$-CH_2-CH_2-\left[O-\overset{O}{\underset{\|}{C}}-(CH_2)_5\right]_m$$

wherein m denotes an integer of 1 to 6;

a, b and c independently of one another represent a real number of 3 or less, provided that they satisfy the conditions of $0 < a \leq 3$, $0 \leq b$ and/or $c < 3$ and $a+b+c=3$.

which shows permanent antistatic property by introducing therein an acrylate moiety having quaternary ammonium group and hydroxy group simultaneously, and to a process for preparing thereof.

6 Claims, No Drawings

PHOTO-CURABLE PREPOLYMER COMPRISING QUATERNARY AMMONIUM SALT AND PROCESS FOR PREPARING THEREOF

BACKGROUND OF INVENTION

1. Field of Invention

The present invention relates to a photo-curable prepolymer comprising quaternary ammonium salt. More specifically, the present invention relates to a photo-curable prepolymer which shows a permanent antistatic property by introducing therein to an acrylate moiety having a quaternary ammonium group and a hydroxy group simultaneously.

The present invention also relates to a process for preparing the photo-curable prepolymer as mentioned above.

2. Background Art

Generally, minute electronic parts used for electric or electronic equipment, household electric appliances, etc., are contained in a plastic case. However, such a plastic case has a tendency to be stained easily by adsorbing dusts which are dispersed through atmosphere since it has static electricity due to the high insulation resistance. Moreover, dusts or static electricity may cause an erroneous operation of the electronic parts. Therefore, it has been recognized that it is essential to finish the electronic parts housing so that any static electricity may not occur.

The early stage anti-static agents, however, are conventionally composed of low molecular weight surfactants. Such an anti-static agent forms a surface layer during coating of a plastic product, but it does not show a durable effect because the anti-static layer can easily be washed out. Accordingly, various processes for applying a surface of a plastic finishing product made from anti-static, curable coating materials having durable antistatic effects have been developed.

For example, European Patent Publication No. 0 541 289 A1 discloses a method for the preparation of a polyurethane prepolymer having a quaternary ammonium salt. This Patent also teaches that a difunctional urethane acrylate latex or water-dispersions thereof can be produced by using the prepolymer and that the thus produced latex can be used as a photo-curable coating material. But, the above Patent focuses merely on a chemical structure of the cationic polyurethane to increase the water-dispersibility of the prepolymer, and there is no mention on an anti-static effect.

In addition, an UV curable antistatic hard-coatings manufactured from polymeric antistatic agents and conventional UV curable coating materials are described in Radtech Asia '93 (P492-498, Nov. 10–13, 1993). However, this cannot be applied practically because the mechanical strength of the UV curable antistatic hard-coatings becomes weaker than that of the early-stage coating materials due to the low cross-linking density. Thus, it has been required to develop a new prepolymer which shows a permanent antistatic property and simultaneously is useful for manufacturing of non-solvent type photo-curable coating material.

Accordingly, the present inventors have focussed their attention on this point and have extensively studied for a long time. As a result, they found an astonishing fact that a photo-curable coating material prepared from a specific prepolymer, i.e., an aliphatic trifunctional urethane acrylate prepolymer made from hydroxy alkyl acrylate having a quaternary ammonium salt, shows a permanent antistatic property and an excellent staining resistance, and thus completed the present invention.

Therefore, it is an object of the present invention to provide an aliphatic trifunctional urethane acrylate prepolymer useful for preparing a photo-curable resin composition.

It is another object of the present invention to provide a process for preparing the photo-curable prepolymer as mentioned above.

The foregoing has outlined some of the more pertinent objects of the present invention. These objects should be construed to be merely illustrative of some of the more pertinent features and applications of the invention. Many other beneficial results can be obtained by applying the disclosed invention in a different manner or modifying the invention within the scope of the disclosure. Accordingly, other objects and a more thorough understanding of the invention may be had by referring to the disclosure of invention, in addition to the scope of the invention defined by the claims.

DISCLOSURE OF INVENTION

In one aspect, the present invention relates to a photo-curable aliphatic trifunctional urethane acrylate prepolymer having the following formula (I):

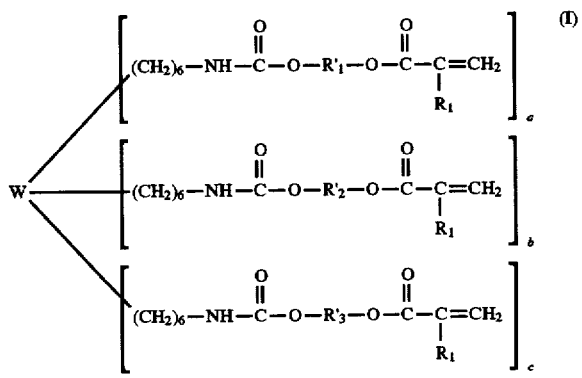

in which

W represents

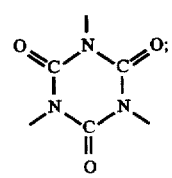

$R_1$ represents hydrogen or methyl;

$R_1'$ represents

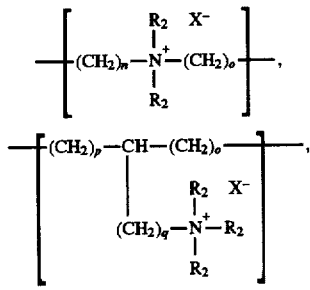

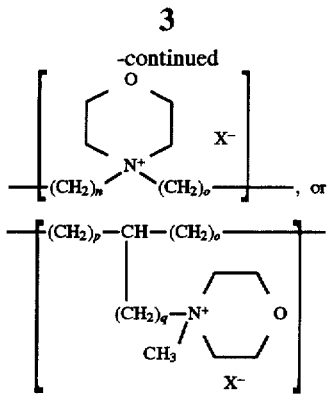

wherein X represents a chlorine or bromine atom, $R_2$ represents methyl or ethyl, n, o and q independently of one another denote an integer of 1 to 6 and p denotes an integer of 0 to 6;

$R_2'$ and $R_3'$ are identical to or different from each other and represent

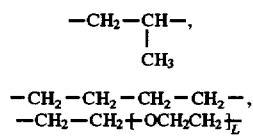

wherein L denotes an integer of 0 to 5, or

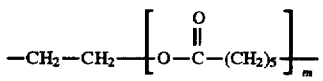

wherein m denotes an integer of 1 to 6;

a, b and c independently of one another represent a real number of 3 or less, provided that they satisfy the conditions of $0 < a \leq 3$, $0 \leq b < 3$ and/or $0 \leq c < 3$ and $a+b+c=3$.

In the second aspect, the present invention relates to a process for preparation of the photo-curable prepolymer of the above formula (I) by reacting an aliphatic multifunctional isocyanate having the following formula (II) with a quaternary ammonium salt having the following formula (III), optionally with the compound of the following formula (IV) and/or that of the following formula (V).

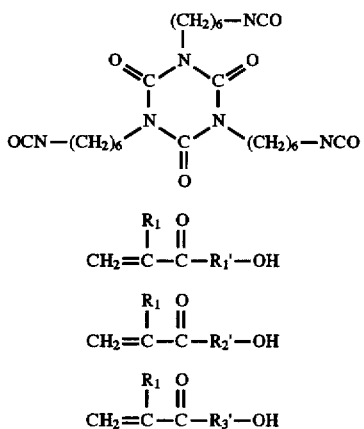

In the above formulas, $R_1$, $R_1'$, $R_2'$ and $R_3'$ are defined as previously described.

The aliphatic multifunctional isocyanate of formula (II) which can-be used in this reaction includes isocyanurate-type trimers of isophorone diisocyanate or hexamethylene diisocyanate. Among them, isocyanurate type trimer of hexamethylene diisocyanate is more preferable, and as its commercially available articles, Luxate HT2000 (Olin Corp.) and Coronate HX (Nippon Polyurethene Ind. Co., Ltd.) can be mentioned.

One of the most important characteristics of the photo-curable prepolymer according to the present invention is that the quaternary ammonium salt of formula (III) is introduced therein. The quaternary ammonium salt of formula (III) has a quaternary ammonium group and a hydroxy group. Among these two groups, the quaternary ammonium group contributes to improving the antistatic property and staining resistance of the finally produced coating material, and the hydroxy group is reacted with the isocyanate functional group of formula (II) to produce the desired prepolymer.

In order to improve the physicochemical properties such as flexibility or adhesion strength, etc. of the photo-cured resin composition which can be prepared from the prepolymer according to the present invention, it is preferable that the compounds of formulae (IV) and/or (V) are mixed with the quaternary ammonium salt of formula (III) and then the mixture is reacted with the aliphatic multifunctional isocyanate of formula (II) to prepare the aliphatic trifunctional urethane acrylate prepolymer of formula (I).

The compounds of formulas (IV) and (V) are hydroxyalkyl methacrylate (or hydroxyalkyl acrylate) compounds which have methacryl (or acryl) and hydroxy functional groups in their structure and at the same time do not include any quaternary ammonium Salts. These compounds (IV) and (V) are optionally used to control the physicochemical properties (for example, flexibility) of the prepolymer (I) according to the present invention. The compounds of formulas (IV) and (V) used herein include hydroxyethyl (meth)acrylate, hydroxypropyl(meth)acrylate or hydroxybutyl acrylate, however, they are not restricted only to these.

As their commercially available articles, hydroxyethyl acrylate, hydroxypropyl acrylate, Sipomer HEM (Rhone-Poulene), Placcel (Daicel Chemical Ind., Ltd.) and Tone Monomer (Union Carbide Co.) can be mentioned.

It is preferable to use the total hydroxy groups which exist in the compounds of formulae (III), (IV) and (V) in a ratio of 1:1 equivalents with respect to the isocyanate groups in the compound of formula (II). It is also preferable to use the hydroxy group in the compound of formula (III) in a ratio of 1/10 to 2/3 equivalents with respect to the isocyanate groups in the compound of formula (II). There is no restriction on the ratio between the amount of the compounds (III), (IV) and (V) used, that is, on the ratio between a, b and c in the formula (I), but it is preferable that a is 0.3 to 2.0 when the sum of a, b and c is 3. In case a exceeds 2.0, there can occur some deterioration in the flexibility and gloss of the product.

By introducing the prepolymer prepared according to the present method into the photo-curable resin composition, a permanent antistatic property and improved staining resistance of the product can be obtained.

The present invention will be more specifically explained in the following examples. However, it should be understood that the following preparations and examples are intended to illustrate the present invention and not to limit the scope of the present invention in any manner.

EXAMPLE 1

Synthesis of methacryloxyethyldimethyl(hydroxyethyl) ammonium bromide 31.4 g (0.2 mole) of (dimethylamino)ethyl methacrylate was introduced into a 250 ml three-neck flask equipped with ice-bath, thermometer, refluxing condenser, dropping funnel and magnetic stirring bar. The compound was stirred and then the temperature was lowered to −10° C. 25 g (0.2 mole) of bromoethanol was added dropwise thereto over 30 minutes while maintaining the temperature of the contents at 0° C. or less. After completion of the addition, the reaction mixture was stirred for 24 hours at room temperature. 100 ml of ethyl acetate was added to the mixture and the whole was stirred, filtered and dried to obtain 54 g (Yield: 96%) of the title compound as a white powder.

$^1$H NMR (DMSO-$d_6$, 300 MHz): δ6.18(1H), 5.85(t,J=1.5 Hz,1H), 5.43(t,J=5.1,1H), 4.63(br.s,2H), 3.95(br.m, 2H), 3.88(br.m,2H), 3.62(br.t,J=5.4,4.5 Hz, 2H), 3.26(s,6H), 2.0 (s,3H)

EXAMPLE 2

74.50 g (0.264 mole) of methacryloxyethyldimethyl (hydroxyethyl) ammonium bromide prepared in Example 1, 204.3712 g (1.76 mole) of hydroxyethyl acrylate and 211.904 g (0.616 mole) of caprolactone modified hydroxyethyl acrylate (Tone M-100; UCC Co.) were mixed together to produce a monomer mixture. On the other hand, 473.2392 g (0.800 mole) of isocyanurate-type trimer of 1,6-hexamethylene diisocyanate (Coronate-HX; Nippon Polyurethene Ind. Co., Ltd.), 0.048 g of dibutyl tin dilaurate as a catalyst and 0.241 g of octadecyl-3-(3,5-di-tertbutyl-4-hydroxyphenyl)propionate (Irganox 1076: Ciba-Geigy Co.) as a radical scavenger were introduced into a reactor equipped with a thermometer, and the temperature of the contents was controlled at 50° C. while stirring at a rate of 200 rpm. After the temperature was equilibrated, the previously prepared monomer mixture was added dropwise thereto over 2 hours with air bubbling, during which the reaction temperature was maintained at less than 60° C. After addition, the temperature of the contents was elevated to 80° C. and 0.096 g of dibutyl tin dilaurate was added thereto and then the mixture was reacted for more than 2 hours. 0.048 g (about 50 ppm) of TNPP (tris(nonylphenyl) phosphite) was added as a stabilizer for completing the reaction, and consequently about 964 g of the prepolymer of which weight percent of NCO group is 0.0 (ASTM D 2572-80) and the Number Average Molecular Weight is 1970 (GPC, measured by CHCl$_3$) was obtained.

$^1$H NMR (CDCl$_3$, 300 MHz): δ4.3(—COOCH$_2$CH$_2$OCO—), 3.5 (CH$_3^+$NCH$_3$Br$^-$), 3.2–3.0(—NHCOO—), 2.2–2.3 (—CH$_2$COO—)

EXAMPLE 3

225.8 g (0.8 mole) of methacryloxyethyldimethyl (hydroxyethyl) ammonium bromide prepared in Example 1 and 255.5 g (2.2 mole) of hydroxyethyl acrylate were mixed together to produce a monomer mixture. On the other hand, 591.55 g (1.0 mole) of isocyanurate-type trimer of 1,6-hexamethylene diisocyanate (Coronate-HX; Nippon Polyurethene Ind. Co., Ltd.), 0.05 g of dibutyl tin dilaurate as a catalyst and 0.27 g of octadecyl-3-(3,5-di-tertbutyl-4-hydroxyphenyl)propionate (Irganox 1076.: Ciba-Geigy Co.) as a radical scavenger were introduced into a reactor equipped with a thermometer, and the temperature of the contents was controlled at 50° C. while stirring at a rate of 200 rpm. After the temperature was equilibrated, the previously prepared monomer mixture was added dropwise thereto over 2 hours with bubbling air, during which the reaction temperature was maintained at less than 60° C. After addition, the temperature of the contents was elevated to 80° C. and 0.1 g of dibutyl tin dilaurate was added thereto and then the mixture was reacted for more than 2 hours. 0.05 g (about 50 ppm) of TNPP (tris(nonylphenyl)phosphite) was added as a stabilizer for completing the reaction, and consequently about 1073 g of the prepolymer of which weight percent of NCO group is 0.0 (ASTM D 2572-80) and the Number Average Molecular Weight is 1520 (GPC, measured by CHCl$_3$) was obtained.

$^1$H NMR (CDCl$_3$, 300 MHz): δ4.3(—COOCH$_2$CH$_2$OCO—), 3.5 (CH$_3^+$NCH$_3$Br$^-$), 3.2–3.0(—NHCOO—)

COMPARATIVE EXAMPLE 1

306 g (2.6 mole) of hydroxyethyl acrylate and 227 g (0.66 mole) of caprolactone modified hydroxyethyl acrylate were mixed together to produce a monomer mixture. On the other hand, 591.55 g (1.0 mole) of isocyanurate-type trimer of 1,6-hexamethylene diisocyanate (Coronate-HX; Nippon Polyurethene Ind. Co., Ltd.), 0.05 g of dibutyl tin dilaurate as a catalyst and 0.27 g of octadecyl-3-(3,5-di-tertbutyl-4-hydroxyphenyl)propionate (Irganox 1076: Ciba-Geigy Co.) as a radical scavenger were introduced into a reactor equipped with a thermometer, and the temperature of the contents was controlled at 50° C. while stirring at the rate of 200 rpm. After the temperature was equilibrated the previously prepared monomer mixture was added dropwise thereto over 2 hours with air bubbling, during which the reaction temperature was maintained at less than 60° C. After addition, the temperature of the contents was elevated to 80° C. and then the mixture was reacted for more than 2 hours. 0.05 g (about 50 ppm) of TNPP (tris(nonylphenyl) phosphite) was added as a stabilizer for completing the reaction, and consequently about 1124 g of the prepolymer of which weight percent of NCO group is 0.0 (ASTM D 2572-80) and the Number Average Molecular Weight is 2220 (GPC, measured by CHCl$_3$) was obtained.

$^1$H NMR (CDCl$_3$, 300 MHz): δ4.3(—COOCH$_2$CH$_2$OCO—), 3.2–3.0 (—NHCOO—), 2.2–2.3(—CH$_2$COO—)

APPLICATION EXAMPLE 1

50 g of the prepolymer prepared in Example 2, 25 g of hydroxyethyl acrylate, 15 g of hexanediol diacrylate, 5 g of trimethylolpropane triacrylate, 4 g of 1-hydroxycyclohexyl phenyl ketone (trademark Irgacure 184; Ciba-Geigy Co.) as a photoinitiator and 1 g of polyether modified dimethylsiloxane copolymer (trademark BYK-307; BYK-Chemie GmbH) as a levelling agent were thoroughly mixed together to prepare a photo-curable resin composition. A glass plate was coated with that resin composition in a thickness of 10 μm and cured with 80 W/cm light from a medium pressure mercury lamp of conventional UV equipment. The cured resin film was peeled from the glass plate. The physicochemical properties of thus obtained free-standing cured film are described in the following Table 1.

APPLICATION EXAMPLE 2

50 g of the prepolymer prepared in Example 3, 25 g of hydroxyethyl acrylate, 15 g of hexanediol diacrylate, 5 g of trimethylolpropane triacrylate, 4 g of 1-hydroxycyclohexyl phenyl ketone (trademark Irgacure 184; Ciba-Geigy Co.) as a photoinitiator and 1 g of polyether modified dimethylsiloxane copolymer (trademark BYK-307; BYK-Chemie GmbH) as a levelling agent were thoroughly mixed together to prepare a photo-curable resin composition. A glass plate was coated with that resin composition in a thickness of 10 μm and cured with 80W/cm light from a medium pressure mercury lamp of conventional UV equipment. The cured resin film was peeled from the glass plate. The physicochemical properties of thus obtained free-standing cured film are described in the following Table 1.

APPLICATION EXAMPLE 3

5 g of the prepolymer prepared in Example 2, 45 g of the prepolymer prepared in Comparative Example 1, 25 g of hydroxyethyl acrylate, 15 g of hexanediol diacrylate, 5 g of trimethylolpropane triacrylate, 4 g of 1-hydroxycyclohexyl phenyl ketone (trademark Irgacure 184; Ciba-Geigy Co.) as a photoinitiator and 1 g of polyether modified dimethylsiloxane copolymer (trademark BYK-307 ; BYK-Chemie GmbH) as a levelling agent were thoroughly mixed together to prepare a photo-curable resin composition. A glass plate was coated with that resin composition in a thickness of 10 μm and cured with 80W/cm light from a medium mercury lamp of conventional UV equipment. The cured resin film was peeled from the glass plate. The physicochemical properties of thus obtained free-standing cured film are described in the following Table 1.

APPLICATION EXAMPLE 4

50 g of the prepolymer prepared in Comparative Example 1, 25 g of hydroxyethyl acrylate, 15 g of hexanediol diacrylate, 5 g of trimethylolpropane triacrylate, 4 g of 1-hydroxycyclohexyl phenyl ketone (trademark Irgacure 184; Ciba-Geigy Co.) as a photoinitiator and 1 g of polyether modified dimethylsiloxane copolymer (trademark BYK-307; BYK-Chemie GmbH) as a levelling agent were thoroughly mixed together to prepare a photo-curable resin composition. A glass plate was coated with that resin composition in a thickness of 10 μm and cured with 80W/cm light from a medium pressure mercury lamp of conventional UV equipment. The cured resin film was peeled from the glass plate. The physicochemical properties of thus obtained free-standing cured film are described in the following Table 1.

TABLE 1

|  | Appln. EX.1 | Appln. EX.2 | Appln. EX.3 | Appln. EX.1 |
|---|---|---|---|---|
| Prepolymer used | EX.2 | EX.3 | COM.EX.1 + EX.2 | COM.EX.1 |
| Surface Resistance (Ω) Initial | $10^{12}$ | $10^{11}$ | $10^{13}$ | $10^{16}$ |
| After 2 months | $10^{12}$ | $10^{11}$ | $10^{13}$ | $10^{16}$ |
| Electrostatic Decay Time (mili second, 50% Cut Off) | 0.2 | 0.1 | 0.5 | $>10^5$ |
| Flexibility (mm) | 3.2 | 3.2 | 3.2 | 3.2 |
| Adhesion Strength | 100/100 | 100/100 | 100/100 | 100/100 |
| Staining Resistance | 1 | 1 | 1 | 2 |

* Note:
Surface Resistance: ASTM D-257
Electrostatic Decay Time: 5kV DC Charge
Flexibility: Minimum diameter at which the test sample does not break by Cylindrical Mandrel Test (ASTM D-522)
Staining Resistance: Scribble on the coated glass plate using an oil magic marker and wipe it out by tissue paper. Then, determine the staining level. There remains no traces (1); there remains some traces (2); and the scribble is not erased (3).
Adhesion Strength: Cut 100 crosshatch lines on the coated polyvinylchloride sheet in a width of 1 mm and then calculate the number of coating layers which remain on the plate after detaching them from the plate using adhesive tape.

What is claimed is:

1. A photo-curable prepolymer having the following formula (I)

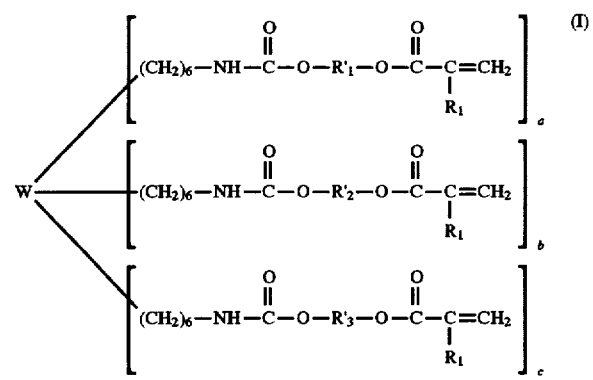

in which

W represents

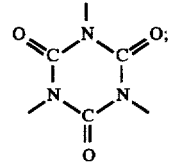

$R_1$ represents hydrogen or methyl;

$R_1'$ represents

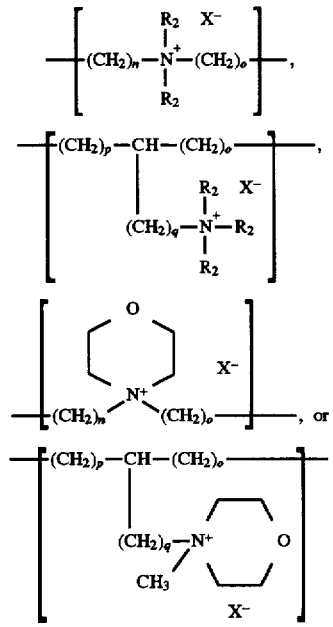

wherein X represents a chlorine or bromine atom, $R_2$ represents methyl or ethyl, n, o and q independently of one another denote an integer of 1 to 6 and p denotes an integer of 0 to 6;

$R_2'$ and $R_3'$ are identical to or different from each other and represent

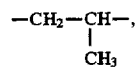

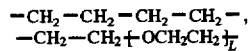

wherein L denotes an integer of 0 to 5, or

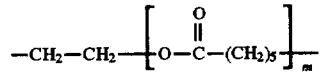

wherein m denotes an integer of 1 to 6;

a, b and c independently of one another represent a real number of 3 or less, provided that they satisfy the conditions of $0 < a \leq 3$, $0 \leq b < 3$ and $0 \leq c < 3$ and $a+b+c=3$.

2. A process for preparing the photo-curable prepolymer of formula (I) as defined in claim 1, comprising reacting an aliphatic multifunctional isocyanate having the following formula (II)

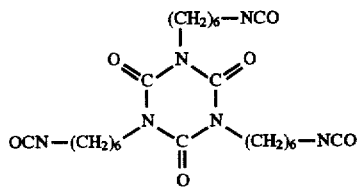

with at least one quaternary ammonium salt selected from salts having the following formulae (III), (IV) and (v):

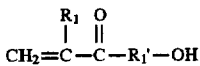

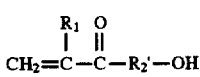

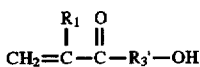

wherein $R_1$, $R_1'$, $R_2'$ and $R_3'$ are defined as described in claim 1.

3. The process according to claim 2, wherein the salt of the formula (IV) or (V) is selected from the group consisting of hydroxyethyl acrylate, hydroxyethyl methacrylate, hydroxypropyl acrylate, hydroxypropyl methacrylate and hydroxypolyester acrylate.

4. The process according to claim 2, wherein the hydroxy group in the compound of formula (III) is used in a ratio of 1/10 to 2/3 equivalents with respect to the isocyanate groups in the compound of formula (II).

5. A cured resin film made by the process of claim 4 and having a surface resistance of from $10^{11}$ to $10^{13}$ $\Omega$ and an electrostatic decay time of from 0.1 to 0.5 milliseconds.

6. A method for preparing a cured resin film having antistatic properties, comprising:

(i) coating a substrate with a resin composition comprising a prepolymer according to claim 1; and (ii) photo-curing said resin composition; to obtain a cured resin film having a surface resistance of from $10^{11}$ to $10^{13}$ $\Omega$ and an electrostatic decay time of from 0.1 to 0.5 milliseconds.

* * * * *